United States Patent [19]
Hileman

[11] Patent Number: 5,191,890
[45] Date of Patent: Mar. 9, 1993

[54] ULTRASONIC PROBE ASSEMBLY

[75] Inventor: Ronald E. Hileman, Lewistown, Pa.

[73] Assignee: Interspec, Inc., Ambler, Pa.

[21] Appl. No.: 689,185

[22] Filed: Apr. 22, 1991

[51] Int. Cl.$^5$ .............................................. A61B 8/12
[52] U.S. Cl. .......................... 128/662.06; 128/661.01
[58] Field of Search ...................... 128/660.03, 661.01, 128/662.03-662.06

[56]  References Cited
U.S. PATENT DOCUMENTS

| | | | |
|---|---|---|---|
| 4,272,991 | 6/1981 | Cribbs | 73/621 |
| 4,374,525 | 2/1983 | Baba | 128/662.06 |
| 4,401,123 | 8/1983 | Baba | 128/662.06 |
| 4,483,326 | 11/1984 | Yamaka et al. | 128/4 |
| 4,543,960 | 10/1985 | Harui et al. | 128/662.06 |
| 4,756,313 | 7/1988 | Terwilliger | 128/662.06 X |
| 4,757,823 | 7/1988 | Hofmeister et al. | 128/662.06 X |
| 4,834,102 | 5/1989 | Schwarzchild et al. | 128/662.06 |
| 4,930,515 | 6/1990 | Terwilliger | 128/662.06 |
| 4,967,752 | 11/1990 | Blumenthal et al. | 128/662.06 X |
| 5,050,610 | 9/1991 | Oaks et al. | 128/660.01 |

FOREIGN PATENT DOCUMENTS 38296039 8/1989 Fed. Rep. of Germany .

OTHER PUBLICATIONS

"An Endoscopic Micromanipulator for Multiplanar Transesophageal Imaging", by Roy W. Martin et al. Ultrasound in Medicine and Biology, vol. 12, No. 12, pp. 965-975, Dec. 1986.
"Esophageal Echocardiography" by Leon Frazin et al., Circulation, vol. 54, No. 1, pp. 102-108 (Jul. 1976).
"Transoesophageal Gross-Sectional Echorardiography with a Phased Array Tran. System" by M. Schluter et al., Transoesophageal 2D echo,48; 67-72 (Jul. 1982).
"A Transesophageal Ultrasound Sector Scanner for Oblique Scans" by K. Hisanaga et al. Abstract of the 52nd Scientific Sessions II-14 245.

Primary Examiner—Francis Jaworski
Attorney, Agent, or Firm—Ratner & Prestia

[57]  ABSTRACT

An ultrasonic probe assembly in which the disposition of the scan plane of an ultrasonic transducer unit, introduced into a human body, can be selected to image a body part in different ways. The scan plane is selected by operation of a remote control unit by which the ultrasonic array is moved. The ultrasonic array is connected to a base unit by means of a flexible coupling and is steered by the action of cables which are controlled by the remote control unit.

31 Claims, 3 Drawing Sheets

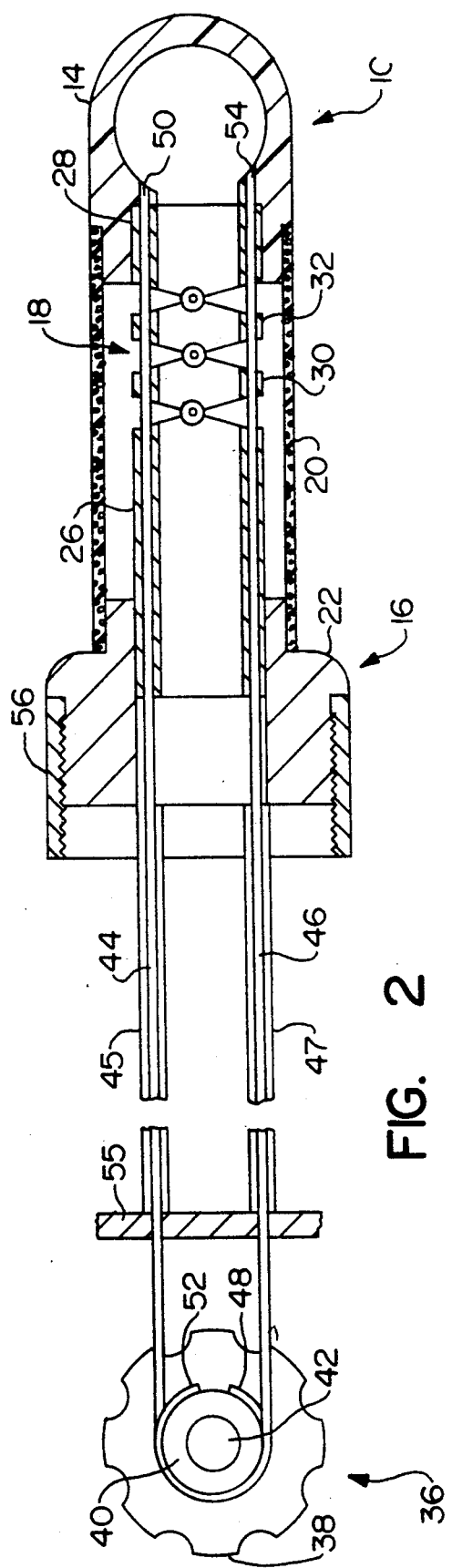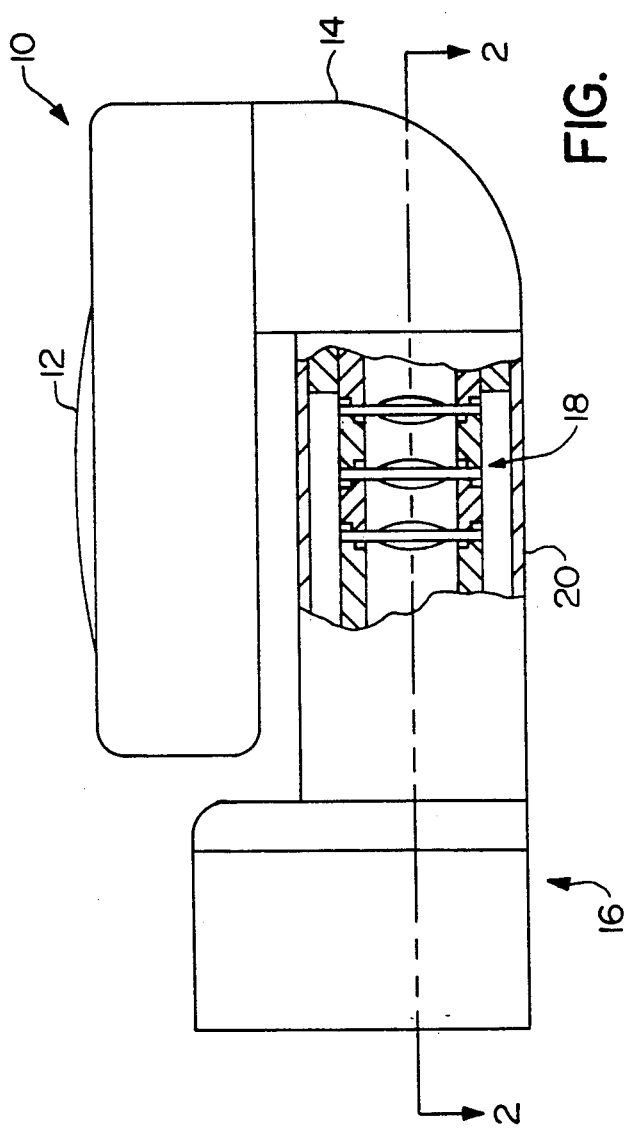

ULTRASONIC PROBE ASSEMBLY

BACKGROUND OF THE INVENTION

The present invention relates, in general, to ultrasonic imaging and, in particular, to a probe in which the scan plane of an ultrasonic transducer unit can be changed, so that a body organ, such as the heart, which is being imaged can be viewed in different ways (i.e. in longitudinal and transverse sections or any section inbetween). Such a probe often is referred to as a "multi-plane" probe by those skilled in the art. Many different ultrasonic multi-plane probes have been suggested or put into actual use in the past. Typically, in these probes, the ultrasonic transducer unit is positioned in a cavity in a housing with the cavity filled with a fluid and covered by a membrane. The ultrasonic probes described and illustrated in U.S. Pat. Nos. 4,543,960 and 4,930,515 are representative of such probes. The scan plane of the ultrasonic array in the probe in U.S. Pat. No. 4,543,960, for example, is changed by operating a cable and pulley mechanism.

There are at least four shortcomings with the prior art ultrasonic multi-plane probes know to applicant. One is size. Although, these probes are small to begin with, even smaller probes are highly desirable.

A second problem with the prior art ultrasonic multi-plane probes known to applicant is the very presence of the fluid in the cavity and the potential damage to the ultrasonic array caused by swelling or corrosion due to the presence of the fluid in the cavity. The fluid is provided in such probes to establish the proper acoustic coupling from the array into the membrane.

A third problem with the prior art ultrasonic multi-plane probes known to applicant is that the membrane cover, which is an added component in the acoustic path, can attenuate and distort sound waves in a manner which reduces ultrasound system resolution.

A fourth problem with such prior art ultrasonic multi-plane probes is that the positioning mechanism passes through sliding seals which are susceptible to leakage of body fluids into the probe cavity to contaminate the fluid in the probe cavity possibly leading to corrosion and acoustic problems. Leakage of the probe cavity fluid into the patient also can occur, but this is problem is overcome by using a biocompatible fluid in the probe cavity.

SUMMARY OF THE INVENTION

An ultrasonic probe assembly, constructed in accordance with the present invention, includes ultrasonic transducer means for scanning in a scan plane and movable through a positioning angle which extends in a plane perpendicular to the scan plane to change the disposition of the the scan plane. The ultrasonic probe assembly of the present invention further includes a base unit, a flexible coupling extending between the base unit and the ultrasonic transducer means and a flexible tube also extending between the base unit and the ultrasonic transducer means and within which the flexible coupling extends. Also included in the ultrasonic probe assembly of the present invention are a remote control unit for selecting an angular position of the ultrasonic transducer means corresponding to a selected disposition of the scan plane and position control means extending from the remote control unit through the base unit and the flexible tube to the ultrasonic transducer means and responsive to the remote control unit for moving the ultrasonic transducer means to the selected angular position.

In one preferred embodiment of the present invention which is described in this application, the ultrasonic transducer means include an ultrasonic array and an array mount upon which the ultrasonic array is mounted. It will be understood, however, that the underlying concept of the present invention can be applied to probes having transducers which are scanned mechanically.

BRIEF DESCRIPTION OF THE DRAWINGS

FIG. 1 is a side view, partially in section, of the probe portion of one preferred embodiment of an ultrasonic probe assembly constructed in accordance with the present invention.

FIG. 2 includes a horizontal section taken along line 2—2 of FIG. 1 and a plan view of the remote control unit portion of a preferred embodiment of an ultrasonic probe assembly constructed in accordance with the present invention.

DETAILED DESCRIPTION OF THE INVENTION

Referring to FIGS. 1 through 5, one preferred embodiment of an ultrasonic probe assembly, constructed in accordance with the present invention, includes an ultrasonic array unit 10 which, in turn, includes an ultrasonic array 12 and an array mount 14 upon which the ultrasonic array is mounted. Ultrasonic array 12 can be of conventional construction and operation, preferably a multi-element phased array ultrasonic transducer, which emits an ultrasonic beam which is scanned in a plane projecting out of the paper for FIGS. 3, 4 and 5. Ultrasonic array 12 is shown by dot-dash lines in FIGS. 3, 4 and 5. As shown in FIG. 2, array mount 14 is, for the embodiment of the invention being described, in the form of a right-angle elbow.

Figure 5:
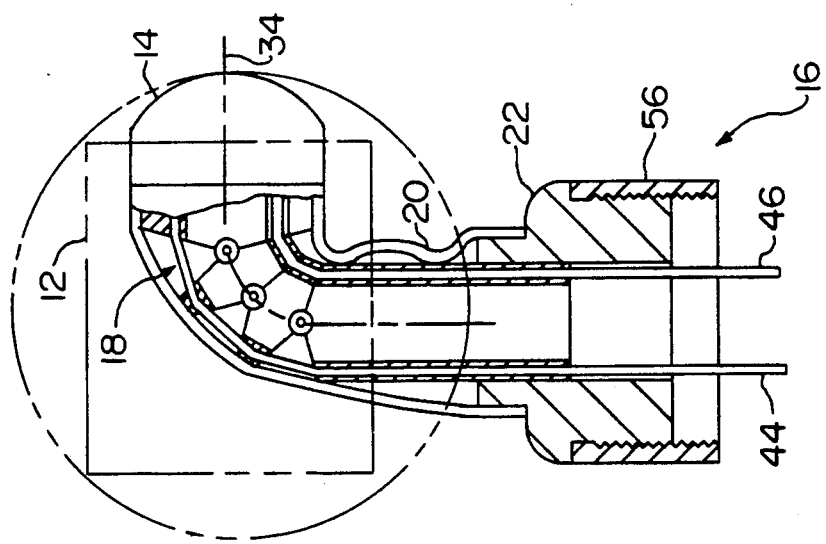
FIGS. 3, 4 and 5 are plan views, on an enlarged scale and partially in section, of three angular positions of the probe portion of the ultrasonic probe assembly of FIGS. 1 and 2.
Figure 4:
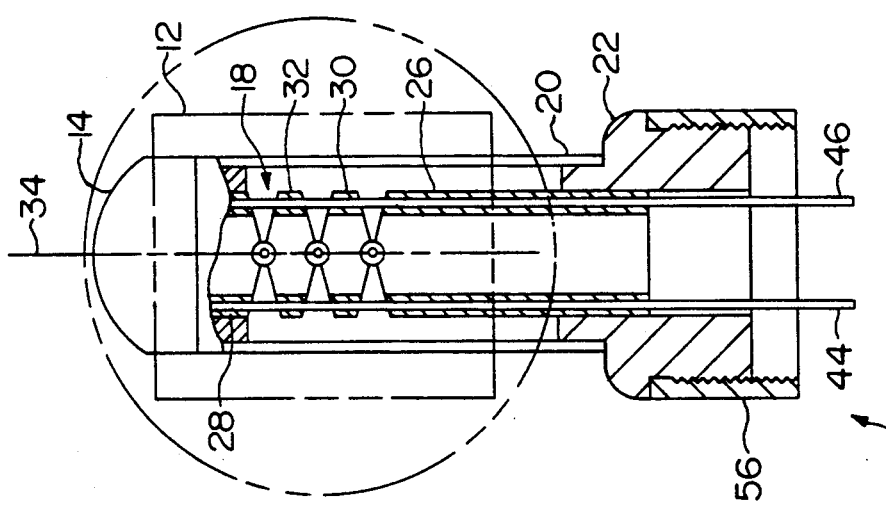
Figure 3:
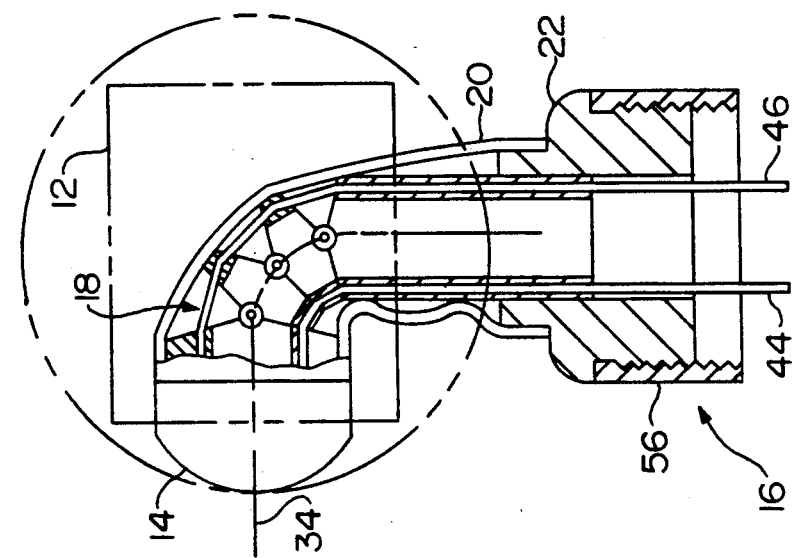

Ultrasonic array unit 10 is movable through a positioning angle which extends in a plane perpendicular to the scan plane of ultrasonic array 12, namely in the plane of the paper for FIGS. 3, 4 and 5, to change the disposition of the scan plane. As shown most clearly in FIGS. 3, 4 and 5, for the embodiment of the invention being described, ultrasonic array 12 can move ninety degrees to the left (FIG. 3) from its center position (FIG. 4) and ninety degrees to the right (FIG. 5) from its center position. This movement of ultrasonic array 12 is generally rotational (i.e. clockwise or counterclockwise).

An ultrasonic probe assembly, constructed in accordance with the present invention, also includes a base unit 16, a flexible coupling 18 and a flexible tube 20. Base unit 16 is in the form of an externally threaded fitting 22 which can be one end of an endoscope, such as the one illustrated in FIG. 6.

Flexible coupling 18 extends between fitting 22 of base unit 16 and elbow 14 of ultrasonic array unit 10 and provides the means by which the ultrasonic array unit and, therefore, ultrasonic array 12, is connected to the base unit. Flexible coupling 18 is composed of a plurality of pivotally connected links which pivot relative to one another about axes disposed perpendicular to the plane in which the positioning angle of ultrasonic array 12 extends, namely out of the paper for FIGS. 3, 4 and 5. Specifically, a first link 26, at a first end of flexible coupling 18, is press-fit into fitting 22 to rigidly attach the flexible coupling to base unit 16 and a second link 28, at a second end of the flexible coupling, is press-fit into elbow 14 to rigidly attach the flexible coupling to ultrasonic array unit 10. For the embodiment of the invention being described, flexible coupling 18 has two additional links 30 and 32. More or less links can be used depending upon the mechanical considerations of the desired design.

As shown in FIGS. 3, 4 and 5, the pivot axes of the pivotally connected links 26, 28, 30 and 32 are disposed along a center line 34 which is: (a) straight when ultrasonic array unit 10 is at the center of the positioning angle of ultrasonic array 12 (FIG. 4); (b) curved in a first direction when ultrasonic array 12 is to a first (i.e. left) side of the center of the positioning angle (FIG. 3); and (c) curved in a second direction opposite &.o the first direction when ultrasonic array 12 is to a second (i.e. right) side of the center of the positioning angle (FIG. 5).

Flexible tube 20 also extends between fitting 22 of base unit 16 and elbow 14 of ultrasonic array unit 10. The opposite ends of flexible tube 20 are attached by suitable means, such as a water resistant adhesive, to fitting 22 and elbow 14 to totally seal, among other things, flexible coupling 18 which extends through the flexible tube from outside fluids.

An ultrasonic probe assembly, constructed in accordance with the present invention, further includes a remote control unit 36 for selecting an angular position of ultrasonic array unit 10 corresponding to a selected disposition of the scan plane of ultrasonic array 12. For the embodiment of the invention being described, remote control unit 36 includes a knob 38, a pulley 40 and a shaft 42 on which the knob and the pulley are rotatably mounted, so that upon turning the knob to a selected position, the position of the pulley is controlled and the pulley will be turned a corresponding amount.

An ultrasonic probe assembly, constructed in accordance with the present invention, further includes position control means for moving ultrasonic array unit 10 to a selected angular position in response to the setting of remote control unit 36. For the embodiment of the invention being described, the position control means include a first cable 44 slidable within a jacket 45 and a second cable 46 slidable within a jacket 47. The lengths of cables 44 and 46, within flexible coupling 18, extend in a plane parallel to the plane in which the positioning angle of the ultrasonic array extends. A first end 48 of cable 44 is attached to pulley 40 of remote control unit 36 and a second end 50 of cable 44 is attached to elbow 14. A first end 52 of cable 46 is attached to pulley 40 of remote control unit 36 and a second end 54 of cable 46 is attached to elbow 14. Cable 44 extends through fitting 22 of base unit 16 and through links 26, 28, 30 and 32 engaging the links at a first side of center line 34, while cable 46 also extends through fitting 22 of base unit 16 and through links 26, 28, 30 and 32 engaging the links at a second and opposite side of center line 34. Jackets 45 and 47 of cables 44 and 46, respectively, are attached to fitting 22 and a wall 55 of remote control unit 36.

As knob 38 is turned in a first direction (i.e. clockwise), cables 44 and 46, engaging the links at opposite sides of center line 34, steer ultrasonic array unit 10 in the generally rotational first direction (i.e. clockwise) and as knob 38 is turned in a second and opposite direction (i.e. counterclockwise), cables 44 and 46 steer ultrasonic array unit 10 in the generally rotational second and opposite direction (i.e. counterclockwise). In this way, ultrasonic array 12 can be moved to any position between the positions shown in FIGS. 3 and 5 to image a selected body part at a selected scan plane.

Figure 6:
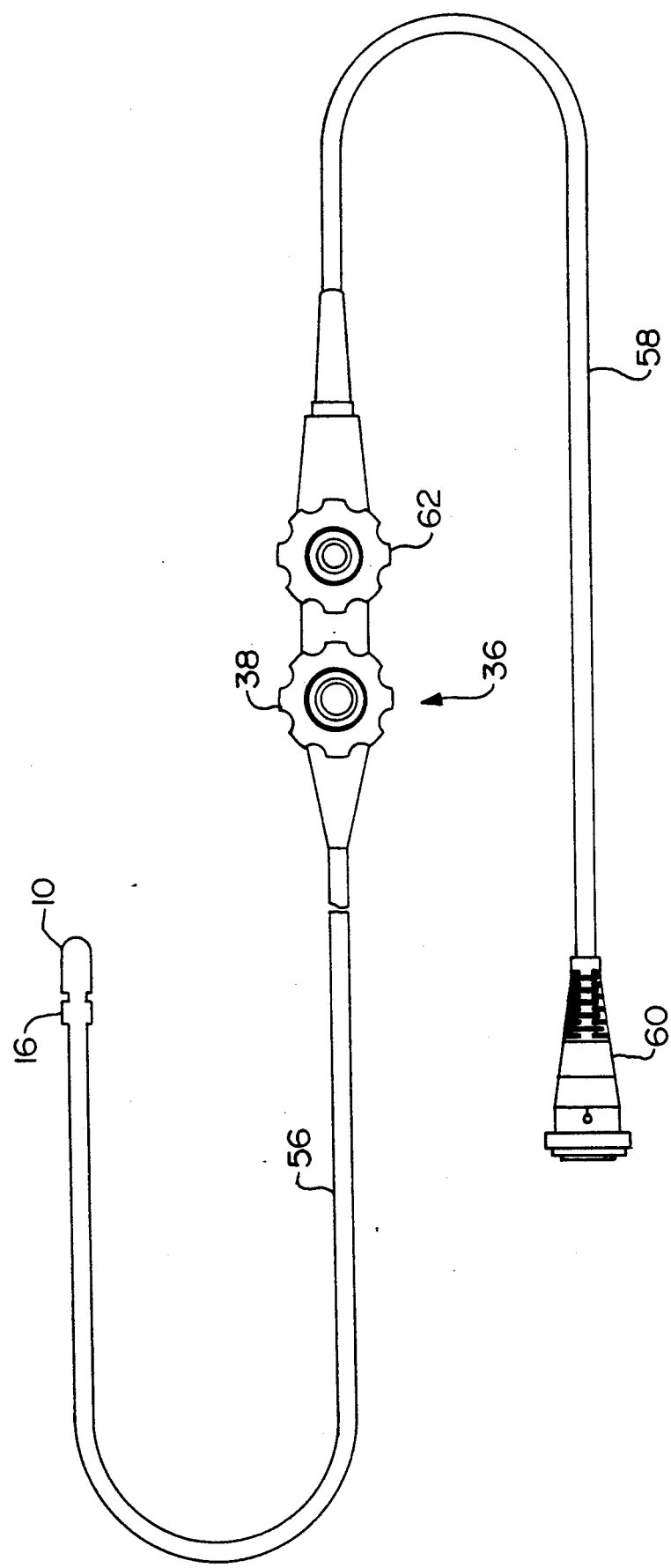
FIG. 6 is a plan view of an endoscope in which the ultrasonic probe assembly of FIGS. 1 through 5 can be incorporated.

FIG. 6 illustrates the ultrasonic probe assembly of FIGS. 1 through 5 incorporated in an endoscope. Ultrasonic array unit 10 and base unit 16 are connected mechanically to remote control unit 36 by cables 44 and 46 (not shown in FIG. 6) and jackets 45 and 47 (not shown in FIG. 6) which extend within a flexible endoscope shaft 56, one end of which is threadedly attached to fitting 22 as shown in FIG. 2. Electrical signals are conducted to and from ultrasonic array unit 10 by wires (also not shown in FIG. 6) which also extend within flexible endoscope shaft 56 and a cable 58 having a connector 60 at one end which is adapted for connection into suitable signal processing and imaging equipment. A second knob 62 on remote control unit 36 controls bending of the end of flexible endoscope shaft 56 upward, downward and sideways to permit the end of the endoscope shaft to make turns as it is passed through the throat.

The foregoing has set forth an exemplary and preferred embodiment of the present invention. It will be understood, however, that various other alternative embodiments will occur to those of ordinary skill in the art with departure from the spirit and scope of the present invention.

What is claimed:

1. An ultrasonic probe assembly comprising:
   an ultrasonic array unit including an ultrasonic array for scanning in a scan plane and an array mount upon which said ultrasonic array is mounted, said ultrasonic array unit movable through a positioning angle extending in a plane perpendicular to said scan plane to change the disposition of said scan plane;
   a base unit;
   a flexible coupling extending between said base unit and said ultrasonic array unit;
   a flexible tube extending between said base unit and said ultrasonic array unit and within which said flexible coupling extends;
   a remote control unit for selecting an angular position of said ultrasonic array unit corresponding to a selected disposition of said scan plane of said ultrasonic array;
   and position control means, including flexible connecting means, extending from said remote control unit through said base unit and said flexible tube to said ultrasonic array unit and responsive to said remote control unit for moving said ultrasonic array unit to said selected angular position, said flexible connecting means having a length which permits positioning said base unit and said ultrasonic array unit within a body cavity of a patient while said remote control unit remains outside the body of the patient.

2. An ultrasonic probe assembly according to claim 1 wherein said flexible coupling includes a plurality of pivotally connected links which pivot relative to one another about axes disposed perpendicular to said plane in which said positioning angle extends.

3. An ultrasonic probe assembly according to claim 2 wherein a first of said pivotally connected links at a first end of said flexible coupling is rigidly attached to said base unit and a second of said pivotally connected links at a second end of said flexible coupling is rigidly attached to said ultrasonic array unit.

4. An ultrasonic probe assembly according to claim 3 wherein said pivot axes of said pivotally connected links are disposed along a center line which is:
    (a) straight when said ultrasonic array unit is at the center of said positioning angle,
    (b) curved in a first direction when said ultrasonic array unit is to a first side of said center of said positioning angle, and
    (c) curved in a second direction opposite to said first direction when said ultrasonic array unit is to a second side of said center of said positioning angle opposite to said first side.

5. An ultrasonic probe assembly according to claim 4 wherein said position control means include first and second cables extending through said flexible coupling in a plane parallel to said plane in which said positioning angle extends:
    (a) said first cable extending from said remote control unit to said array mount and engaging said pivotally connected links at a first side of said center line, and
    (b) said second cable extending from said remote control unit to said array mount and engaging said pivotally connected links at a second side of said center line opposite from said first side of said center line.

6. An ultrasonic probe assembly according to claim 5 wherein said array mount includes a right-angle elbow to which said first and said second cables, said second pivotally connected link and said flexible tube all are attached.

7. An ultrasonic probe assembly according to claim 6 wherein said remote control unit includes:
    (a) a rotatably mounted pulley to which said first and said second cables are connected, and
    (b) a knob connected to said pulley to control the position of said pulley.

8. An ultrasonic probe assembly according to claim 5 wherein said position control means further include first and second cable jackets within which said first and said second cables, respectively, are slidable and said first and said second cable jackets extend between said base unit and said remote control unit.

9. An ultrasonic probe assembly according to claim 1 wherein said ultrasonic array is mounted on said array mount at an edge of said ultrasonic array remote from said base unit.

10. An endoscope comprising:
    an ultrasonic array unit including an ultrasonic array for scanning in a scan plane and an array mount upon which said ultrasonic array is mounted, said ultrasonic array unit movable through a positioning angle extending in a plane perpendicular to said scan plane to change the disposition of said scan plane;
    a base unit;
    a flexible coupling extending between said base unit and said ultrasonic array unit;
    a flexible tube extending between said base unit and said ultrasonic array unit and within which said flexible coupling extends;
    a remote control for selecting an angular position of said ultrasonic array unit corresponding to a selected disposition of said scan plane of said ultrasonic array;
    position control means, including flexible connecting means, extending from said remote control unit through said base unit and said flexible tube to said ultrasonic array unit and said flexible tube to said ultrasonic array unit and responsive to said remote control unit for moving said ultrasonic array unit to said selected angular position, said flexible connecting means having a length which permits positioning said base unit and said ultrasonic array unit within a body cavity of a patient while said remote control unit remains outside the body of the patient;
    and means for connecting said remote control unit to signal processing and imaging equipment.

11. An endoscope according to claim 10 wherein said flexible coupling includes a plurality of pivotally connected links which pivot relative to one another about axes disposed perpendicular to said plane in which said positioning angle extends.

12. An endoscope according to claim 11 wherein a first of said pivotally connected links at a first end of said flexible coupling is rigidly attached to said base unit and a second of said pivotally connected links at a second end of said flexible coupling is rigidly attached to said ultrasonic array unit.

13. An endoscope according to claim 12 wherein said pivot axes of said pivotally connected links are disposed along a center line which is:
    (a) straight when said ultrasonic array unit is at the center of said positioning angle,
    (b) curved in a first direction when said ultrasonic array unit is to a first side of said center of said positioning angle, and
    (c) curved in a second direction opposite to said first direction when said ultrasonic array unit is to a second side of said center of said positioning angle opposite to said first side.

14. An endoscope according to claim 13 wherein said position control means include first and second cables extending through said flexible coupling in a plane parallel to said plane in which said positioning angle extends:
    (a) said first cable extending from said remote control unit to said array mount and engaging said pivotally connected links at a first side of said center line, and
    (b) said second cable extending from said remote control unit to said array mount and engaging said pivotally connected links at a second side of said center line opposite from said first side of said center line.

15. An endoscope according to claim 14 wherein said array mount includes a right-angle elbow to which said first and said second cables, said second pivotally connected link and said flexible tube all are attached.

16. An endoscope according to claim 15 wherein said remote control unit includes:
    (a) a rotatably mounted pulley to which said first and said second cables are connected, and
    (b) a knob connected to said pulley to control the position of said pulley.

17. An endoscope according to claim 10 wherein said ultrasonic array is mounted on said array mount at an edge of said ultrasonic array remote from said base unit.

18. An ultrasonic probe assembly comprising:
   ultrasonic transducer means for scanning in a scan plane and movable through a positioning angle extending in a plane perpendicular to said scan plane to change the disposition of said scan plane;
   a base unit;
   a flexible coupling extending between said base unit and said ultrasonic transducer means;
   a flexible tube extending between said base unit and said ultrasonic transducer means and within which said flexible coupling extends;
   a remote control for selecting an angular position of said ultrasonic transducer means corresponding to a selected disposition of said scan plane;
   and position control means, including flexible connecting means, extending from said remote control unit through said base unit and said flexible tube to said ultrasonic transducer means and responsive to said remote control unit for moving said ultrasonic transducer means to said selected angular position, said flexible connecting means having a length which permits positioning said base unit and said ultrasonic array unit within a body cavity of a patient while said remote control unit remains outside the body of the patient.

19. An ultrasonic probe assembly according to claim 18 wherein said flexible coupling includes a plurality of pivotally connected links which pivot relative to one another about axes disposed perpendicular to said plane in which said positioning angle extends.

20. An ultrasonic probe assembly according to claim 19 wherein said pivot axes of said pivotally connected links are disposed along a center line which is:
   (a) straight when said ultrasonic array unit is at the center of said positioning angle,
   (b) curved in a first direction when said ultrasonic array unit is to a first side of said center of said positioning angle, and
   (c) curved in a second direction opposite to said first direction when said ultrasonic array unit is to a second side of said center of said positioning angle opposite to said first side.

21. An ultrasonic probe assembly according to claim 20 wherein said position control means include first and second cables extending through said flexible coupling in a plane parallel to said plane in which said positioning angle extends:
   (a) said first cable extending from said remote control unit to said array mount and engaging said pivotally connected links at a first side of said center line, and
   (b) said second cable extending from said remote control unit to said array mount and engaging said pivotally connected links at a second side of said center line opposite from said first side of said center line.

22. An ultrasonic probe assembly according to claim 20 wherein said position control means further include first and second cable jackets within which said first and said second cables, respectively, are slidable and said first and said second cable jackets extend between said base unit and said remote control unit.

23. An ultrasonic probe assembly comprising:
   ultrasonic transducer means for forming and scanning an ultrasound beam and movable through a positioning angle extending in a plane perpendicular to the scanning of said ultrasound beam to change the disposition of the scanning of said ultrasound beam;
   a base unit;
   a flexible coupling extending between said base unit and said ultrasonic transducer means;
   a flexible tube extending between said base unit and said ultrasonic transducer means and within which said flexible coupling extends;
   a remote control unit for selecting an angular position of said ultrasonic transducer means corresponding to a selected disposition of the scanning of said ultrasound beam;
   and position control means, including flexible connecting means, extending from said remote control unit through said base unit and said flexible tube to said ultrasonic transducer means and responsive to said remote control unit for moving said ultrasonic transducer means to said selected angular position, said flexible connecting means having a length which permits positioning said base unit and said ultrasonic array unit within a body cavity of a patient while said remote control unit remains outside the body of the patient.

24. An ultrasonic probe assembly comprising:
   a base unit;
   an ultrasonic array unit including an ultrasonic array for scanning in a scan plane and an array mount upon which said ultrasonic array is mounted;
   means for mounting said ultrasonic array unit to said base unit with said ultrasonic array external to said base unit for movement of said ultrasonic array unit through a positioning angle extending in a plane perpendicular to said scan plane of said ultrasonic array to change the disposition of said scan plane;
   a remote control unit for selecting an angular position of said ultrasonic array unit corresponding to a selected disposition of said scan plane of said ultrasonic array;
   and position control means, including flexible connecting means, extending from said remote control unit through said base unit to said ultrasonic array unit and responsive to said remote control unit for moving said ultrasonic array within a body cavity of a patient while said remote control unit remains outside the body of the patient.

25. An ultrasonic probe assembly according to claim 24 wherein said mounting means include:
   (a) a flexible coupling extending between said base unit and said ultrasonic array unit, and
   (b) a flexible tube extending between said base unit and said ultrasonic array unit and within which said flexible coupling extends.

26. An ultrasonic probe assembly according to claim 25 wherein said ultrasonic array is mounted on said array mount at an edge of said ultrasonic array remote from said base unit.

27. An endoscope comprising:
   a base unit;
   an ultrasonic array unit including an ultrasonic array for scanning in a scan plane and an array mount upon which said ultrasonic array is mounted;
   means for mounting said ultrasonic array unit to said base unit with said ultrasonic array external to said base unit for movement of said ultrasonic array unit through a positioning angle extending in a plane perpendicular to said scan plane of said ultrasonic array to change the disposition of said scan plane;

a remote control unit for selecting an angular position of said ultrasonic array unit corresponding to a selected disposition of said scan plane of said ultrasonic array;

position control means, including flexible connecting means, extending from said remote control unit through said base unit to said ultrasonic array unit and responsive to said remote control unit for moving said ultrasonic array unit to said selected angular position, said flexible connecting means having a length which permits positioning said base unit and said ultrasonic array unit within a body cavity of a patient while said remote control unit remains outside the body of the patient;

and means for connecting said remote control unit to signal processing and imaging equipment.

28. An endoscope according to claim 27 wherein said mounting means include:
 (a) a flexible coupling extending between said base unit and said ultrasonic array unit, and
 (b) a flexible tube extending between said base unit and said ultrasonic array unit and within which said flexible coupling extends.

29. An endoscope according to claim 28 wherein said ultrasonic array is mounted on said array mount at an edge of said ultrasonic array remote from said base unit.

30. An ultrasonic probe assembly comprising:
 ultrasonic transducer means for scanning in a scan plane;
 a base unit;
 means for mounting said ultrasonic transducer means to said base unit with said ultrasonic transducer means external to said base unit for movement of said ultrasonic transducer means through a positioning angle extending in a plane perpendicular to said scan plane to change the disposition of said scan plane;
 a remote control unit for selecting an angular position of said ultrasonic transducer means corresponding to a selected disposition of said scan plane;
 and position control means, including flexible connecting means, extending from said remote control unit through said base unit to said ultrasonic transducer means and responsive to said remote control unit for moving said ultrasonic transducer means to said selected angular position, said flexible connecting means having a length which permits positioning has base unit and said ultrasonic array unit within a body cavity of a patient while said remote control unit remains outside the body of the patient.

31. An ultrasonic probe assembly according to claim 30 wherein said mounting means include:
 (a) a flexible coupling extending between said base unit and said ultrasonic transducer means, and
 (b) a flexible tube extending between said base unit and said ultrasonic transducer means and within which said flexible coupling extends.

* * * * *

UNITED STATES PATENT AND TRADEMARK OFFICE
CERTIFICATE OF CORRECTION

PATENT NO. : 5,191,890
DATED : March 9, 1993
INVENTOR(S) : Ronald E. Hileman

It is certified that error appears in the above-indentified patent and that said Letters Patent is hereby corrected as shown below:

Col. 6, lines 11, 12 -   Delete "said flexible tube to said ultrasonic array unit and" (phrase is repeated)

Col. 8, line 44        -   Insert between "array" and "within":  --unit to said selected angular position, said flexible connecting means having a length which permits positioning said base unit and said ultrasonic array unit--

Col. 10, line 19       -   Delete "has" and insert --said--

Signed and Sealed this

Twenty-eighth Day of December, 1993

Attest:

BRUCE LEHMAN

*Attesting Officer*          *Commissioner of Patents and Trademarks*